(12) United States Patent
Philipps et al.

(10) Patent No.: US 7,165,549 B2
(45) Date of Patent: Jan. 23, 2007

(54) NASAL SPRAY

(75) Inventors: Tom Philipps, Darmstadt (DE); Klaus Weber, Leiningen (DE); Olaf Hirsch, Koblenz (DE); Eva-Maria Karow, Niedererbach (DE)

(73) Assignee: Siemen's & Co. und Quellenprodukte des Staatbades, Bad Ems (DE)

( * ) Notice: Subject to any disclaimer, the term of this patent is extended or adjusted under 35 U.S.C. 154(b) by 245 days.

(21) Appl. No.: 10/493,003

(22) PCT Filed: Oct. 16, 2002

(86) PCT No.: PCT/DE02/03913

§ 371 (c)(1),
(2), (4) Date: Oct. 6, 2004

(87) PCT Pub. No.: WO03/034973

PCT Pub. Date: May 1, 2003

(65) Prior Publication Data

US 2005/0045181 A1 Mar. 3, 2005

(30) Foreign Application Priority Data

Oct. 19, 2001 (DE) ................ 101 51 676

(51) Int. Cl.
*A61M 15/08* (2006.01)
(52) U.S. Cl. ............ 128/207.18; 128/207.16; 222/481.5
(58) Field of Classification Search ........ 128/200.14, 128/200.17, 200.18, 200.21, 200.24, 203.12, 128/203.14, 204.12, 207.18, 206.11, 207.16, 128/205.24; 604/289, 290, 313, 315, 316; 222/206, 207, 211, 212, 481.5, 484
See application file for complete search history.

(56) References Cited

U.S. PATENT DOCUMENTS

| 3,089,626 | A | * | 5/1963 | Kubiliunas | 222/484 |
|---|---|---|---|---|---|
| 3,542,256 | A | * | 11/1970 | Waterman | 222/484 |
| 3,812,853 | A | * | 5/1974 | Crain | 128/200.17 |
| 3,847,145 | A | * | 11/1974 | Grossan | 601/160 |
| 5,505,193 | A | * | 4/1996 | Ballini et al. | 128/200.15 |
| 6,238,377 | B1 | * | 5/2001 | Liu | 604/289 |
| 6,484,715 | B1 | * | 11/2002 | Ritsche et al. | 128/200.21 |
| 6,736,792 | B1 | * | 5/2004 | Liu | 604/94.01 |
| 6,793,104 | B2 | * | 9/2004 | Kao | 222/481.5 |
| 2004/0231669 | A1 | * | 11/2004 | Bruna | 128/204.12 |
| 2005/0028812 | A1 | * | 2/2005 | Djupesland | 128/200.21 |
| 2005/0133546 | A1 | * | 6/2005 | Carvalho | 222/481.5 |

FOREIGN PATENT DOCUMENTS

| DE | 3332723 | 3/1985 |
|---|---|---|
| DE | 3929964 | 1/1991 |
| JP | 10017039 | 1/1998 |

* cited by examiner

*Primary Examiner*—Teena Mitchell
(74) *Attorney, Agent, or Firm*—Jan K. Simpson; Fulbright & Jaworski LLP

(57) ABSTRACT

A nasal spray with a container for rinsing fluid, which has a delivery aperture, with a valve body kept movable in the region of the delivery aperture with a tube attached to said valve body, such that different swivel positions of the valve body in co-operation with the delivery aperture determine an open position (FIG. 2), in which the tube is in communication with the container, and a closed position (FIG. 1), in which the container is sealed, wherein the valve body can be swivelled into a ventilation position (FIG. 3) which is different from the open and closed positions, in which the container is ventilated and residue can be emptied.

19 Claims, 7 Drawing Sheets

NASAL SPRAY

CROSS-REFERENCE TO RELATED APPLICATIONS

This is a national stage application of PCT/DE02/03913 filed Oct. 16, 2002, claiming priority to DE 101 51 676.2 filed Oct. 19, 2001.

TECHNICAL FIELD

The invention relates to a nasal spray with a container for rinsing fluid, which has a delivery aperture, with a valve body kept movable in the region of the delivery aperture with a tube attached to said valve body, such that different swivel positions of the valve body in co-operation with the delivery aperture determine an open position, in which the tube is in communication with the container, and a closed position, in which the container is sealed, as is known from DE 39 29 964 C2.

BACKGROUND OF THE INVENTION

The known nasal spray has proven very successful in practice, though it has occasionally turned out to be awkward in use, in that, once filled with rinsing fluid, the spray always has to be held in the hand, since the liquid runs out otherwise. Furthermore, the tube projecting from the container and/or the movable valve body could be damaged.

One object of the invention therefore consists in improving the known nasal spray such that it is easier to handle in use and damage to the valve body or the tube attached to it can be substantially ruled out.

BRIEF SUMMARY OF THE INVENTION

This object is achieved, in accordance with the invention, by a nasal spray according to claim 1. Useful further embodiments of the invention are shown in the dependent claims.

BRIEF DESCRIPTION OF THE DRAWINGS

The invention will now be explained in the light of a working embodiment, reference being made to a drawing, in which.

DETAILED DESCRIPTION OF THE INVENTION

Figure 1:
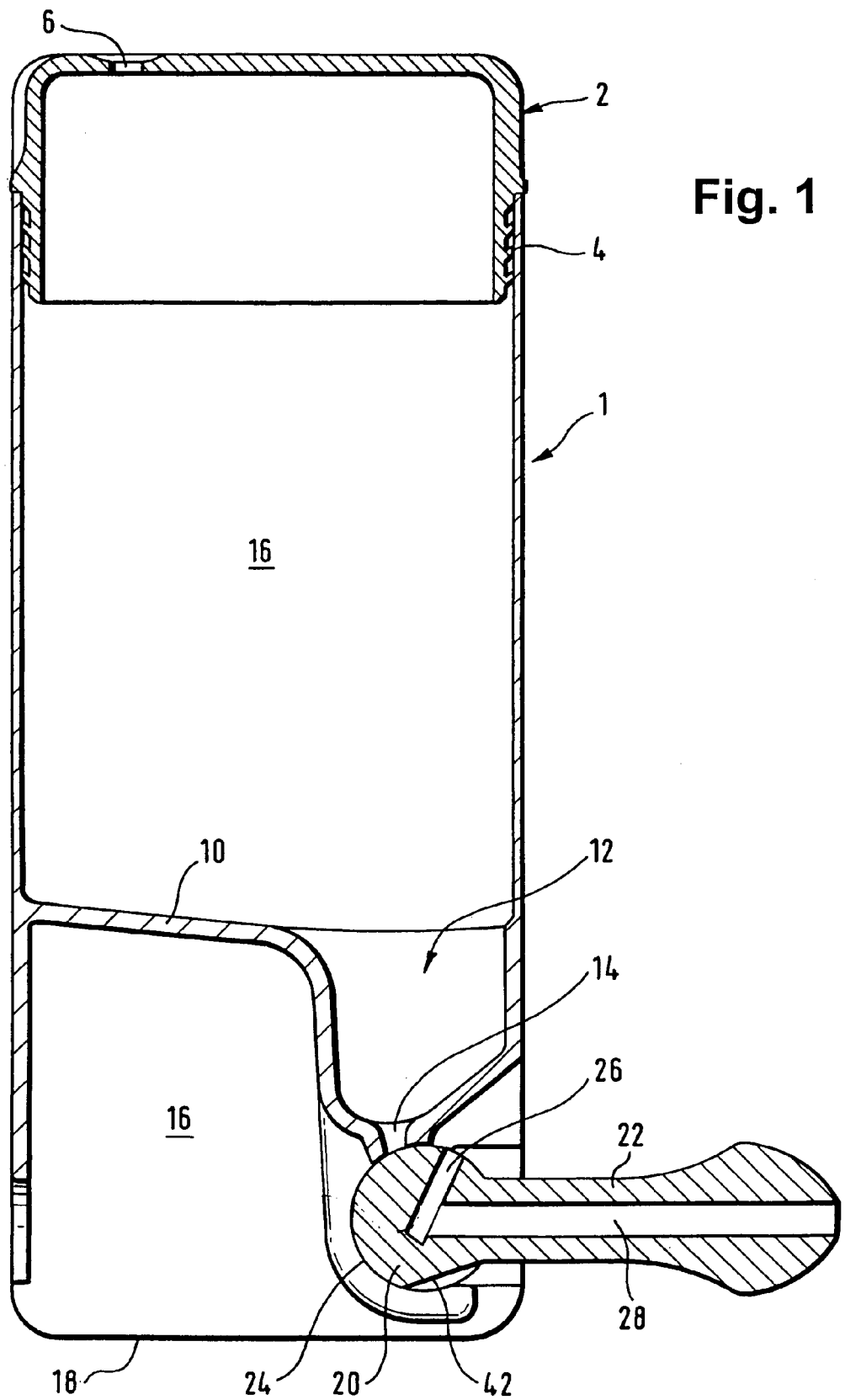
FIG. 1 shows a view of the nasal spray of the invention in cross-section, in the closed position.

Referring first to FIGS. 1 to 4, which show the structure of the nasal spray of the invention and how it works, the nasal spray is shown in the upright or vertical position in which it is used. A substantially cylindrical container 1 is sealed in an air-tight and fluid-tight manner by means of a removable lid 2, which has peripheral sealing lips 4, the lid 2 having a metering aperture 6 which can be temporarily blocked or unblocked with one finger. It can be provided for the lid 2 to co-operate with a sealing and retaining bead of the container by means of a peripheral clamping groove, so that it does not become detached from the container and still forms a tight seal even when internal pressure builds up in the container (metering under pressure, see below). Recessed grips 8 (FIG. 4) formed in the outer side walls 16 of the container facilitate holding the spray and simultaneously closing or opening the metering aperture 6.

Internally, the container terminates approximately in its lower third in a bottom wall 10, which forms an indentation 12 with a dispensing aperture 14 disposed in the bottom-most region of the indentation. The side walls 16 of the container are extended downwards beyond the region the bottom wall 10, so that standing surfaces 18 are formed to set down the container or nasal spray in the (vertical) position shown, i.e. the position for use.

A substantially cylindrical valve body 20 with a tube 22 projecting from it is mounted adjacent to the dispensing aperture 14 such as to be capable of swivelling. The valve body 20 can be moved from the closed to the open position swivelling it by about 30° up to 60° or by about 45° so that the different swivel positions shown in FIGS. 1 to 3 can be adopted.

FIG. 1 shows the closed position of the valve body, in which the dispensing aperture 14 of the container is blocked by a cylindrical outer surface 24 of the valve body 20.

Figure 2:
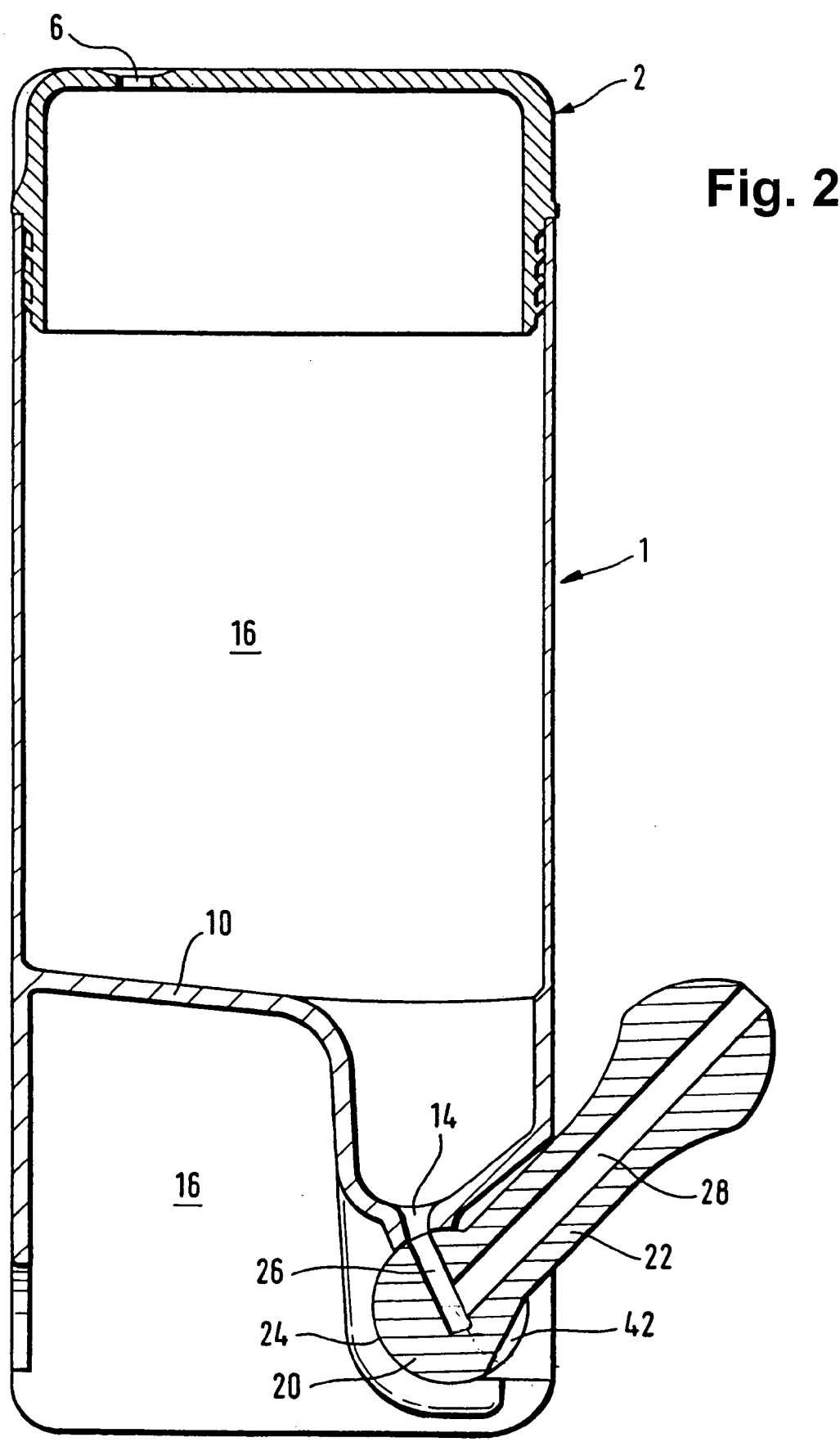
FIG. 2 shows a view in accordance with FIG. 1, in the open position.

FIG. 2 shows the position for use, or open position, wherein a connecting duct 26 disposed substantially radially in the valve body 20 is in communication with the dispensing aperture 14, while a delivery duct 28 running through the valve body and the tube 22 adjoins the connecting duct 26, so that a fluid located inside the container can emerge through the delivery duct 28.

Figure 3:
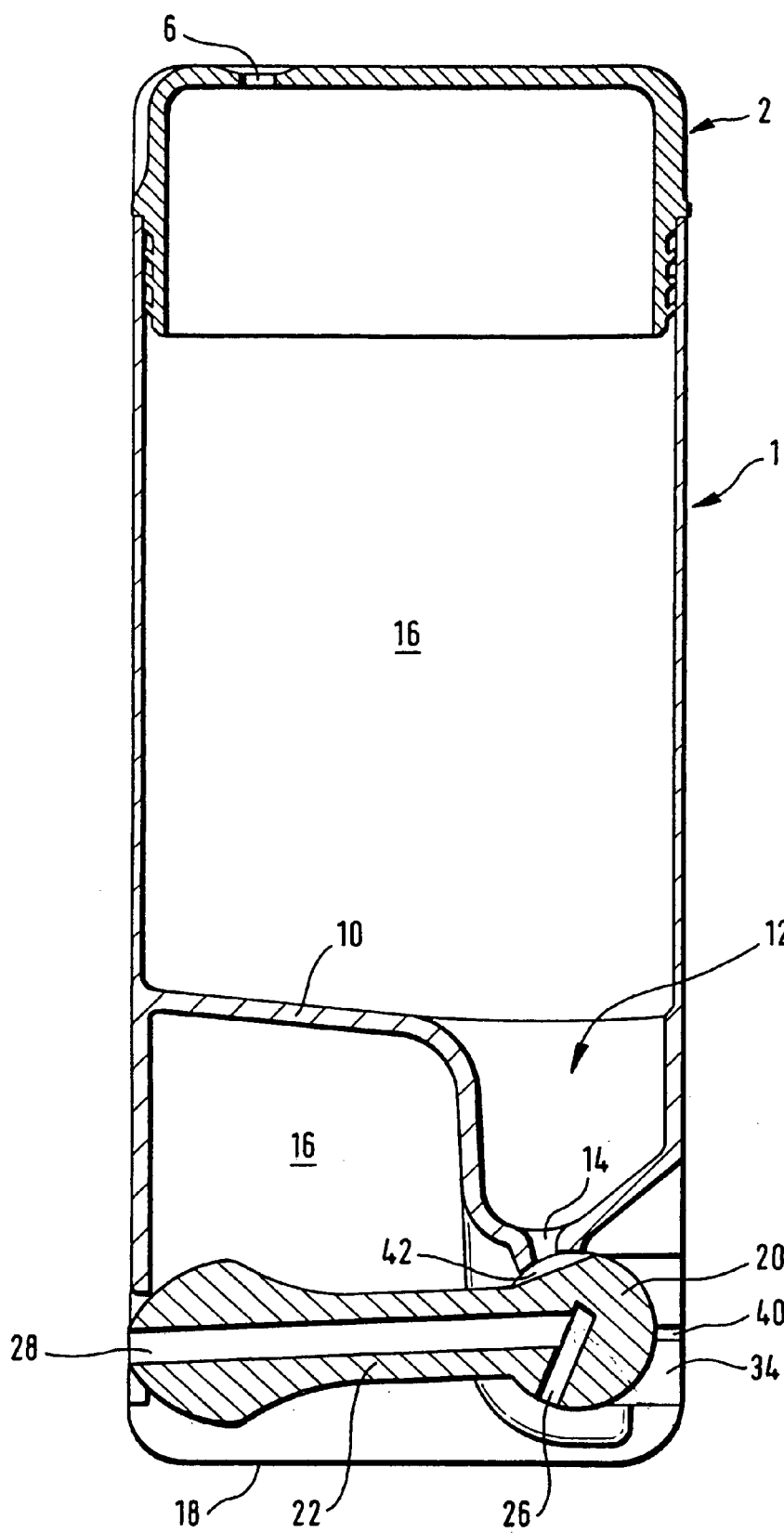
FIG. 3 shows a view in accordance with FIGS. 1 and 2, in the ventilation position.
Figure 4:
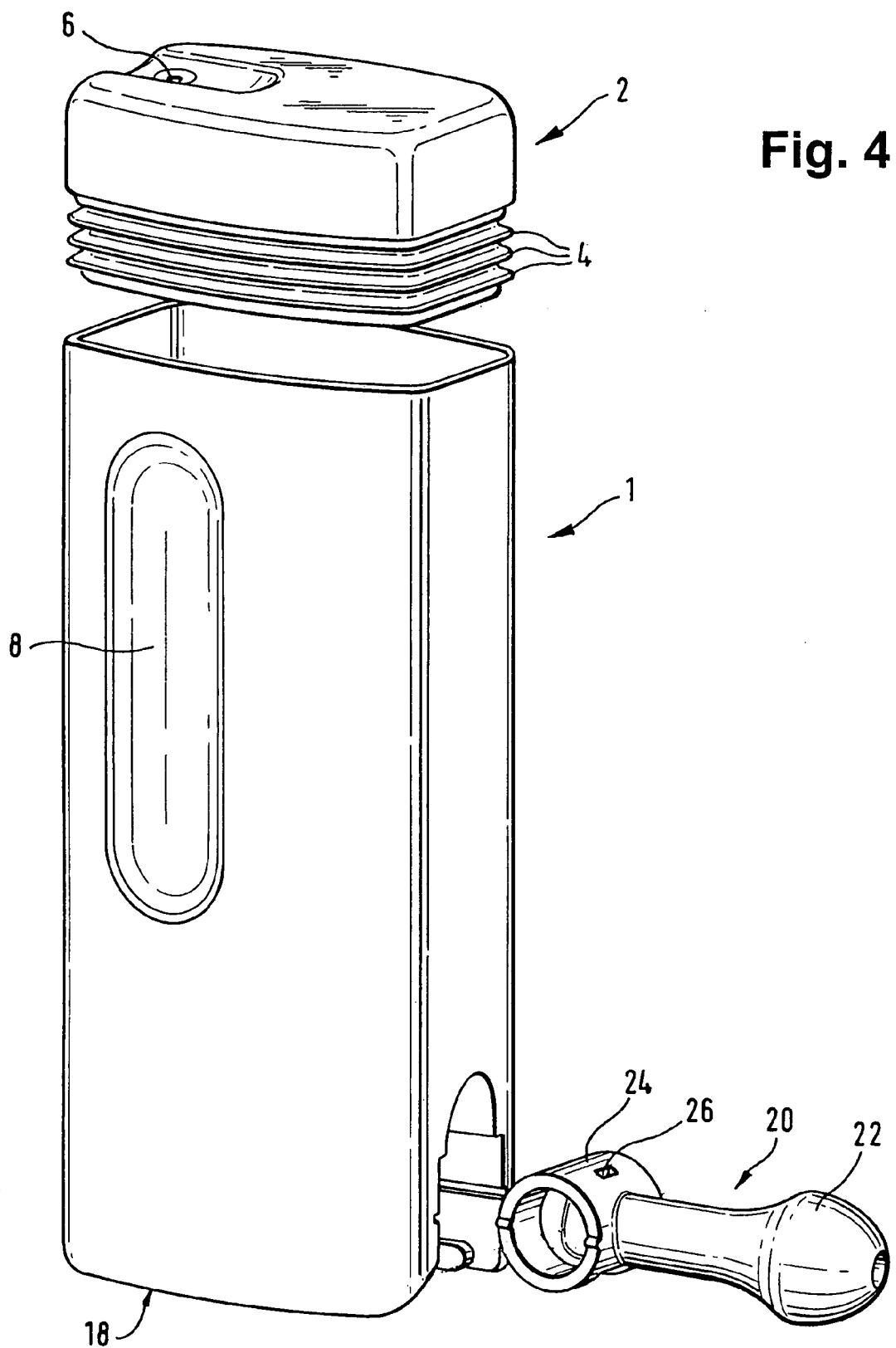
FIG. 4 shows an expanded, perspective view of details of the spray according to the invention.

FIG. 3 shows a ventilation position of the valve body 20, in which the latter has been swivelled so far that the tube 22 connected to it is completely located between the extended side walls 16 and thus no longer projects beyond the cylindrical or approximately block-shaped outer contours of the container 1, but is covered by them.

Figure 5:
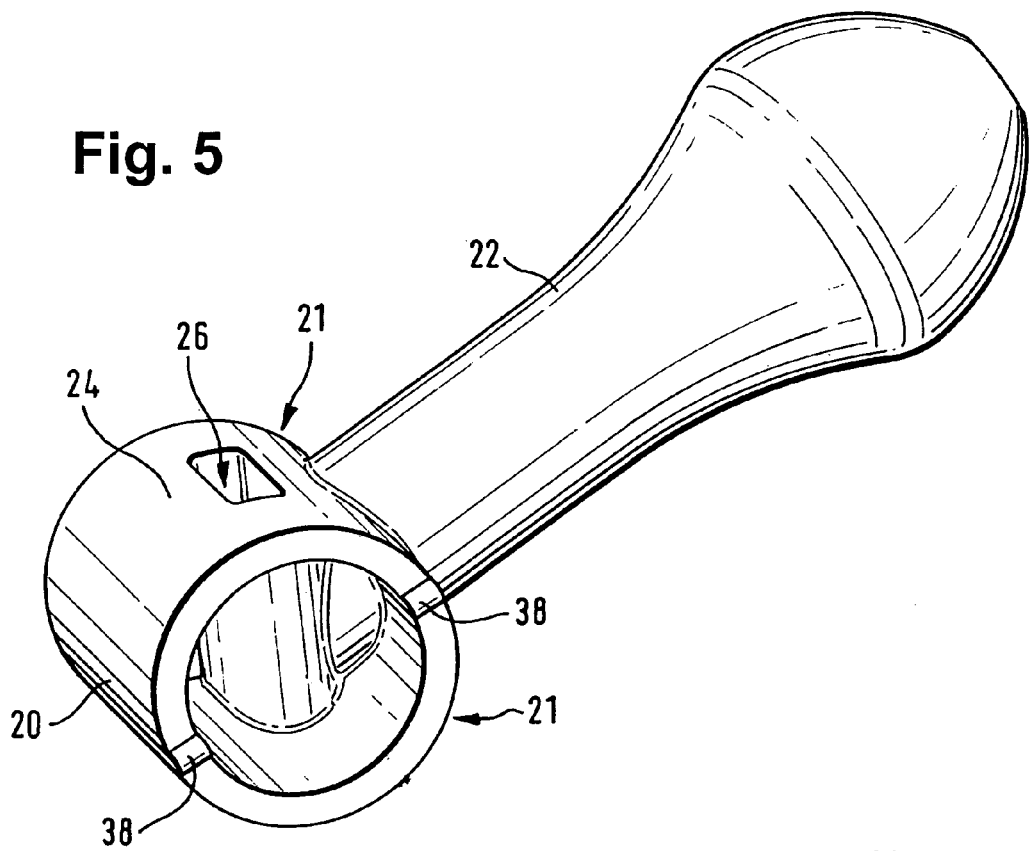
FIG. 5 shows a perspective view of the valve body with the tube attached and FIG. 5a shows a perspective view of the valve body with the tube detached.
Figure 6:
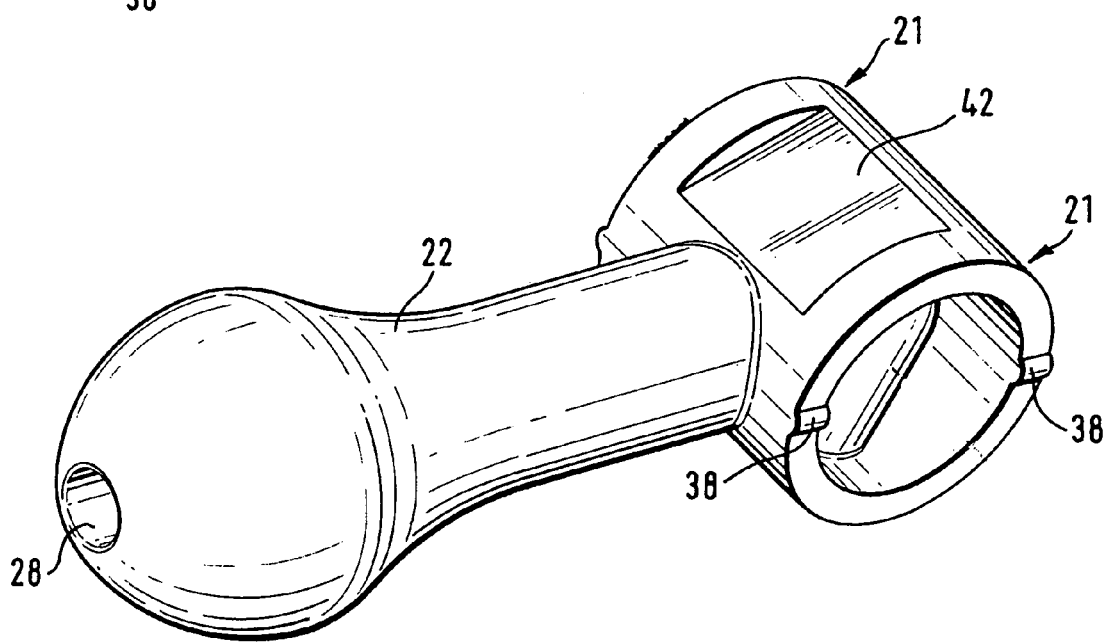
FIG. 6 shows a perspective view of the valve body and tube from a different angle.
Figure 5A:
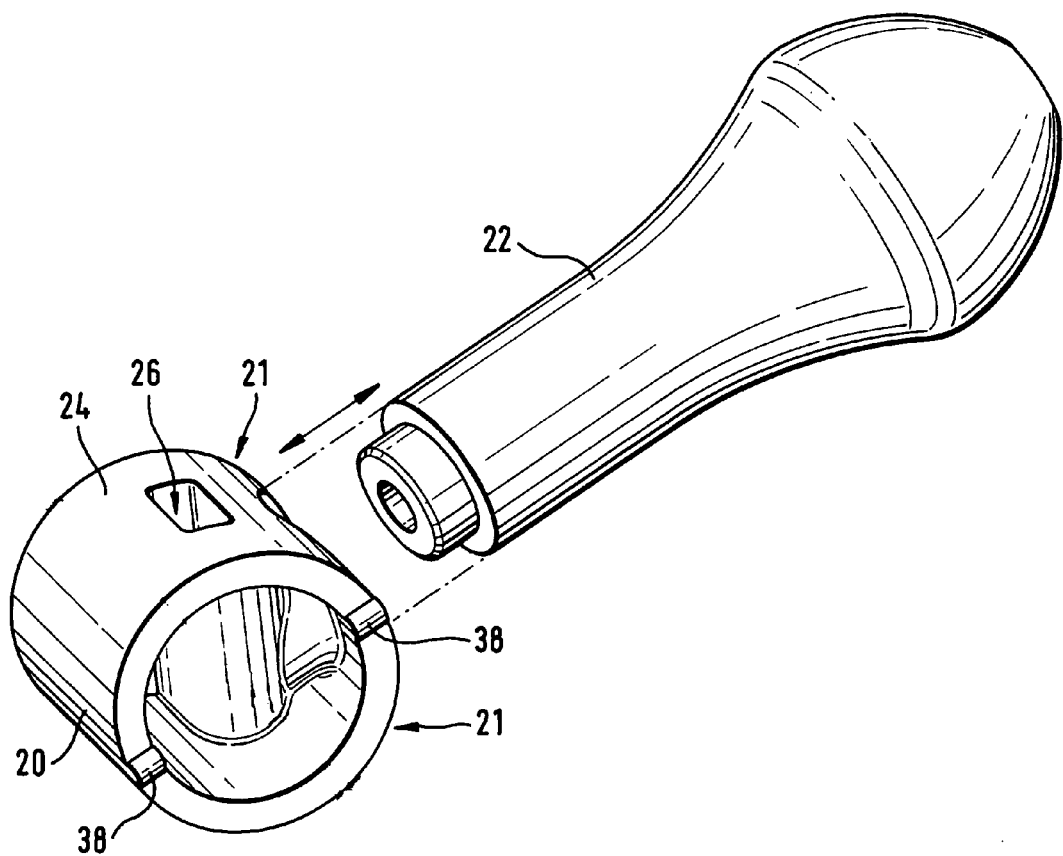

FIGS. 5, 5a and 6 show enlarged views of the valve body 20 and of the associated tube 22, from which the basic hollow cylindrical shape of the valve body can be seen. The tube 22 is formed integrally with the valve body 20 or is designed such as to be capable of being slipped onto the valve body 20. The connecting duct 26 has a rectangular cross-section and corresponds in shape and size approximately to the dispensing aperture 14 (FIGS. 7 and 8) or to the locating face 25 formed around said dispensing aperture 14, which co-operates with the sealing surface 24.

In the lower portion of the container, substantially planar bearing tags 32 are formed on the bottom wall 10 and the side walls 16, which, in the lateral or axial direction (relative to the swivelling axis of the valve body), have planar limiting walls 34 and C-shaped bearing lands 36, extending in the circumferential direction over an angle of more than 180° at the circumference. This design makes it possible for the valve body 20 to lock in against the elastically slightly deformable bearing tags 32 or the bearing lands 36 and to be removed in the opposite direction, so that the valve body can be inserted and removed without breakage.

Alternatively the lateral cylindrical end portions of the valve body 20, which serve as supports, and the bearing lands 36 (or the valve body as a whole) could be designed asymmetrically, e.g. being of different diameters left and right, in order to ensure that the valve body can only be inserted in the correct alignment (and not twisted round by 180°).

Figure 7:
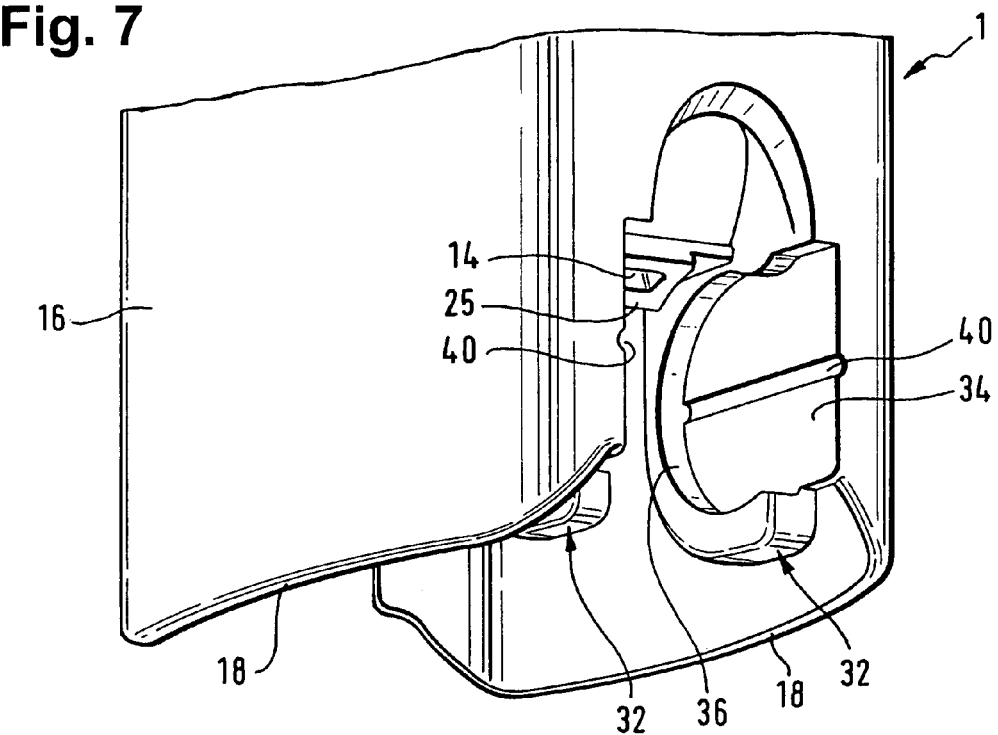
FIG. 7 shows an enlarged perspective view of the region of the nasal spray which receives the valve body.
Figure 8:
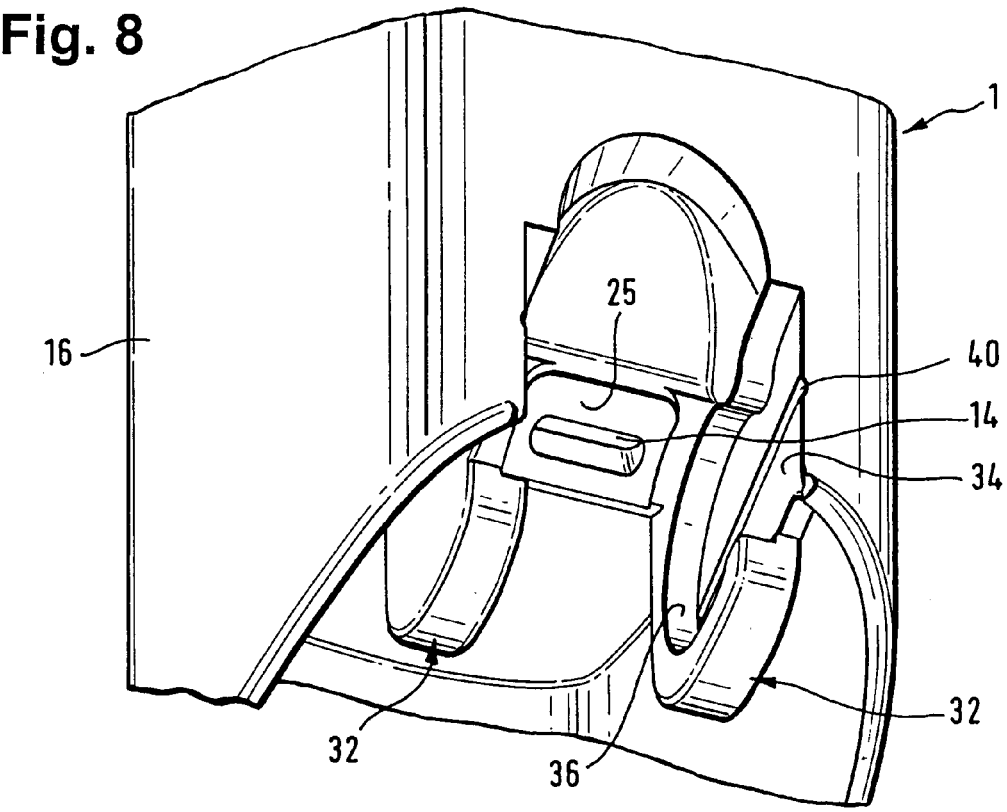
FIG. 8 shows the region according to FIG. 7 from a different direction, in a partially cut-away view.

As FIGS. 5 to 7 also show, the hollow cylindrical end portions or bearing elements 21 of the valve body 20 are equipped with detent lugs 38 which, in the closed position (FIG. 1) and ventilation position (FIG. 3), co-operate with corresponding detent grooves 40 in the limiting walls 34 of the bearing tags 32, so that the valve body 20 is held fixed in those positions and any accidental swivelling into the open position is prevented. Alternatively the detent lugs 38 and detent grooves 40 can also be left out or replaced by detent means of some other design.

As FIGS. 3 and 6 further show, the valve body 20 is equipped with a sloping, tangential shallower portion or recess 42 for emptying residue, which, in the ventilation position (FIG. 3) is opposite the dispensing aperture 14. This ensures that the container 1 in the ventilation position is open at both ends, namely at the metering aperture 6 on the one hand, and the dispensing aperture 14 on the other, and is in communication with the ambient air, which makes ventilation possible and ensures that any residue can be emptied.

For use, the nasal spray is placed in the closed position (FIG. 1), the lid 2 is removed, a desired rinsing fluid is poured in and the lid replaced. The user takes the device in one hand in the vertical alignment shown in the figures of the drawing, and blocks the metering aperture 6, e.g. with his index finger. Following that, the valve body is placed (partially or completely) in the open position (FIG. 2), and the device is ready for use as soon as it has been placed against the nose, the rinsing fluid being metered by (partially) opening the metering aperture 6, so that the rinsing fluid emerges from the tube 22 solely under the force of gravity (hydrostatic pressure). If desired, the pressure can be increased by closing the metering aperture 6 and pressing the container 1 (pressure on the side walls 16).

After use, the valve body is placed in the ventilation position (FIG. 3), as a result of which the dispensing aperture 14 is open, owing to the recess 42 for emptying residue, and any remaining rinsing fluid left in the container 1 can escape freely. In the ventilation position, all the surfaces and ducts of the device which come into contact with rinsing fluid are in communication with the ambient air, namely the container 1, the dispensing aperture 14, the delivery duct 28 and the connecting duct 26.

In order to clean the device thoroughly, the valve body 20, as has already been mentioned, can be removed from its mount and replaced without damage. It is important in this connection that the sealing function (valve body vis-á-vis delivery aperture) is kept separate from the bearing function (valve body vis-á-vis container) by design means, so that even after the valve body has been removed and replaced repeatedly, the sealing function is not impaired.

A further benefit is that the device can be set down on the standing surfaces 18 at the lower end of the side walls 16 in all positions of the valve body 20 (FIGS. 1 to 3), and especially in the closed and ventilation positions, so that handling is improved. The possibility of placing the valve body in the ventilation position offers the advantage that the tube 22 is protected against contamination and damage, the recess 42 for emptying residue serving at the same time to empty the device and to provide ventilation.

LIST OF REFERENCE NUMERALS

1 Container
2 Lid
4 Sealing lip
6 Metering aperture
8 Recessed grip
10 Bottom wall
23 Indentation
14 Dispensing aperture
16 Side wall
18 Standing surface
20 Valve body
21 Bearing element
22 Tube
24 Outer surface (sealing surface)
25 Locating face
26 Connecting duct
28 Delivery duct
32 Bearing tag
34 Limiting wall
36 Bearing land
38 Detent lug
40 Detent groove
42 Recess for emptying residue

What is claimed is:

1. A nasal spray with a container for rinsing fluid, comprising:
    a dispensing aperture, with a valve body kept movable in the region of the dispensing, aperture;
    a tube attached to said valve body, such that different swivel positions of the valve body in co-operation with the dispensing aperture determine an open position; in which the tube is in communication with the container, and a closed position, in which the container is sealed;
    wherein the valve body can be swivelled into a ventilation position which is different from the open and closed positions, whereby the container is ventilated and residue can be emptied.

2. The spray as claimed in claim 1, wherein the container has outer contours overlapping or covering the valve body and tube in the ventilation position, with standing surfaces formed thereon, on which the container can be set down.

3. The spray as claimed in claim 2, wherein the standing surfaces are formed by free end portions of the side walls of the container.

4. The spray as claimed in claim 1, wherein the valve body has a recess for emptying residue, which, in the ventilation position, communicates with the dispensing aperture.

5. The spray as claimed in claim 4, wherein the recess for emptying residue is designed as a bevelled portion of the valve body.

6. The spray as claimed in claim 1, wherein the valve body has a curved sealing surface which co-operates, in the open and closed positions, with the dispensing aperture, and a connecting duct connected to the tube and leading into the sealing surface communicates, in the open position, with the dispensing aperture.

7. The spray as claimed in claim 6, wherein the container has, on the outside and in the region of the dispensing aperture, a locating face with a curvature corresponding to the sealing surface.

8. The spray as claimed in claim 1, wherein first detent members are associated with the valve body, the first detent members co-operate in at least one position, especially the closed and/or ventilation position, with corresponding second detent members of the container and secure the valve body against unintentional swivelling.

9. The spray as claimed in claim 1, wherein the valve body can be moved from the closed to the open position by swivelling it by about 30° up to 60°.

10. The spray as claimed in claim 9, wherein the valve body can be moved from the closed to the open position by swivelling it by about 45°.

11. The spray as claimed in claim 1, wherein the valve body is cylindrical in shape and is equipped with bearing elements in its end portions.

12. The spray as claimed in claim 1, wherein the valve body has cylindrical bearing elements which rest in corresponding bearing recesses in the container.

13. The spray as claimed in claim 12, wherein the bearing elements and bearing recesses are designed to be asymmetrical.

14. The spray as claimed in claim 1, wherein the valve body can be removed from the container and replaced without damage.

15. The spray as claimed in claim 1, wherein the valve body is mounted in lateral bearing tags on the container, which have C-shaped bearing lands extending over an angle of more than 180° at the circumference.

16. The spray as claimed in claim 15, wherein the bearing tags are formed on side walls of the container, between which the valve body and tube can be received in the ventilation position.

17. The spray as claimed in claim 1, wherein the tube is formed integrally with the valve body or is designed such as to be capable of being slipped onto the valve body.

18. The spray as claimed in claim 1, wherein the container is provided with a tight-sealing lid having a metering aperture.

19. The spray as claimed in claim 18, wherein the lid is retained on the container in such a way that it provides a tight seal when there is internal pressure.

* * * * *